United States Patent [19]

Barker et al.

[11] 4,096,739

[45] Jun. 27, 1978

[54] PROCESSABILITY TESTER

[75] Inventors: Robert I. Barker, Cuyahoga Falls; David P. King, Akron, both of Ohio

[73] Assignee: Monsanto Company, St. Louis, Mo.

[21] Appl. No.: 825,538

[22] Filed: Aug. 17, 1977

Related U.S. Application Data

[63] Continuation of Ser. No. 736,508, Oct. 28, 1976, abandoned.

[51] Int. Cl.² ............................................. G01N 11/04
[52] U.S. Cl. ........................................... 73/56; 73/15.4
[58] Field of Search ................... 73/54, 56, 15.6, 15.4

[56] References Cited

U.S. PATENT DOCUMENTS

| 3,203,225 | 8/1965 | Sieglaff et al. ............... 73/56 X |
| 3,252,320 | 5/1966 | Welty .............................. 73/56 |
| 3,270,553 | 9/1966 | Ballman et al. .................. 73/56 |
| 3,279,240 | 10/1966 | Kowalski ..................... 73/15.4 |

FOREIGN PATENT DOCUMENTS 18,760  11/1962  Japan ........................... 73/15.4

Primary Examiner—Richard C. Queisser
Assistant Examiner—Joseph W. Roskos

[57] ABSTRACT

Evaluating extrudable material by forcing such material through an outlet of a chamber by means of a movable member then stopping and securing the movable member at a predetermined position and measuring the force on the material as it decays with time.

10 Claims, 8 Drawing Figures

PROCESSABILITY TESTER

This application is a continuation of application Ser. No. 736,508, filed Oct. 28, 1976, now abandoned.

This invention relates to a method and apparatus for evaluating extrudable materials and more particularly for evaluating the processability of elastomers. Still more particularly, the invention provides an improved method and apparatus for determining viscosity and stress relaxation of elastomers.

Stress relaxation is a useful indicator of the behavior of elastomer compositions when subjected to various processes such as extruding, molding and calendering, and is useful to characterize elastomer compositions in terms of dimensional stability, flow throughput, etc. Prior methods of measuring stress relaxation have been by indirect means such as compressing coupled with measurement of the recovery by transducer means or by photographing. Photographing a sample is a static, time-consuming method subject to operator error. Compression methods operate at low shear rates. A necessary requirement for a meaningful processability test is that the shear rates directly relate to those encountered in the actual process. Processing rates are typically in the range of $10 - 10^5 \text{ sec}^{-1}$.

A quick and simple method of evaluating extrudable materials has been discovered which, in effect, comprises determining viscosity from stress on the material at high shear rate and at low shear rate and determining the stress relaxation. A supply of extrudable material is charged to a chamber having an outlet and a movable member for forcing the material through the outlet. The member is moved to extrude material from the outlet as in known procedures for determining viscosity with high shear rate instruments. The improvements comprise stopping the movable member at a predetermined position, securing it in such position and measuring the force as it decays with time. As a preliminary step, viscosity may be evaluated by measuring the force required to extrude the material at a constant rate of extrusion (constant shear rate) or by measuring the time to extrude a predetermined volume of material subjected to constant force (constant shear stress).

The method may be adapted for automatically testing a number of elastomeric samples. For example, the samples may be cut from a sheeted elastomer by a pneumatic press and injected directly into a cassette. After the cassette is filled with samples, it may be placed in an oven until the samples reach equilibrium test temperature, removed from the oven and placed in the tester. The samples are automatically fed to the tester and subjected to the evaluation as described.

Figure 1:
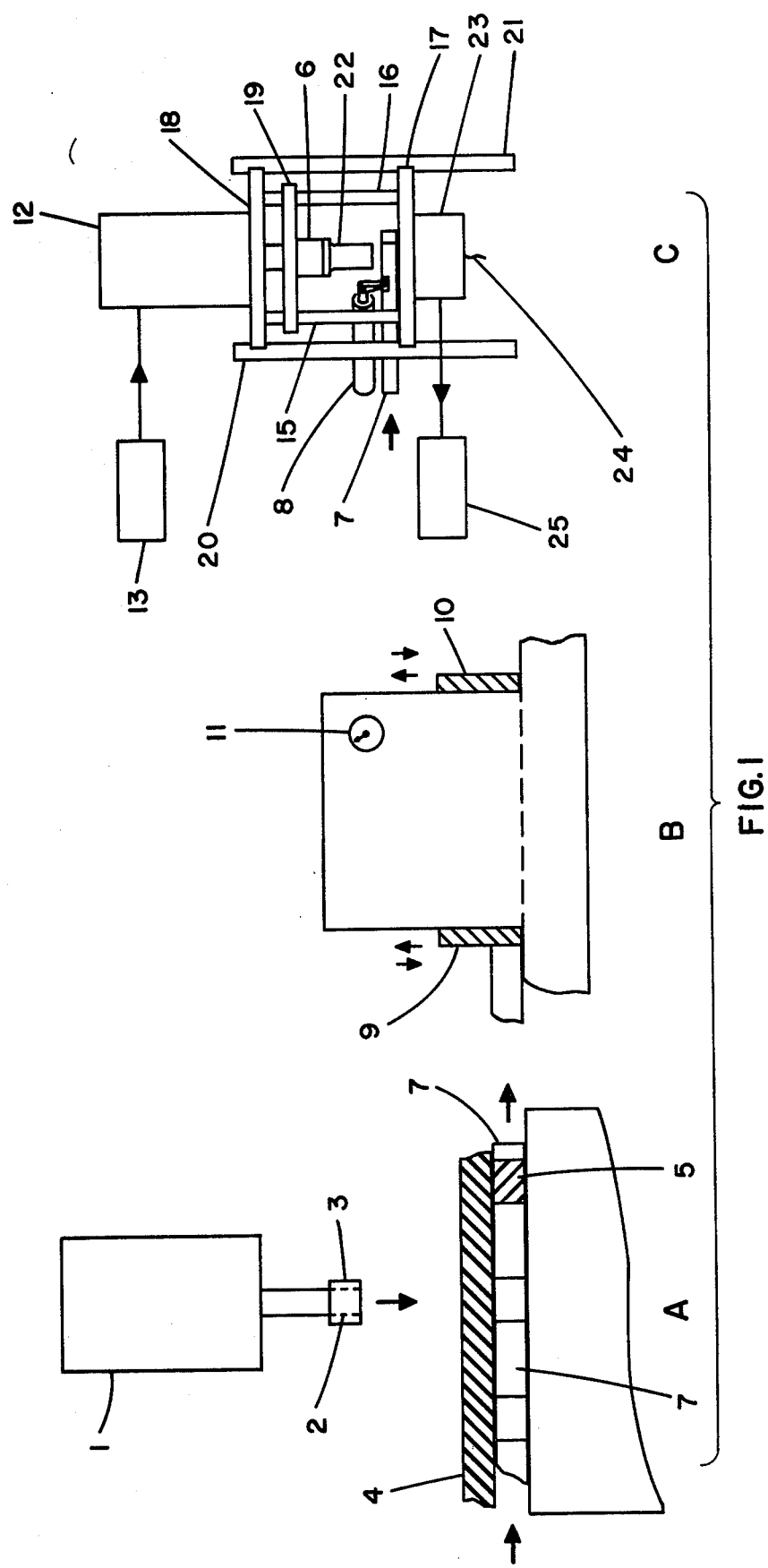
FIG. 1 is a schematic arrangement of an automatic testing system comprising sample cutter, oven and tester.

Referring to FIG. 1, the sample cutter (A) comprises a pneumatic cylinder 1 which operates a plunger 2 at the bottom of which is a circular cutter 3. The assembly is arranged so that the cutter dies out the sample 5 from sheeted elastomer 4 and the plunger injects the sample into the cassette 7. An advance mechanism 8 allows the cavities in the cassette to be accurately aligned with the plunger. The oven B which may be either microwave or electrical heating includes doors 9 and 10 which may be automatically controlled by timer 11 to allow the passage of the sample cassette in a predetermined time. The sample time in the oven should be sufficient to arrive at equilibrium test temperature without sample degredation.

The tester C is preferably a Capillary Rheometer operating under constant shear rate conditions. The drive system 12 for the Capillary Rheometer preferably comprises a closed loop servo hydraulic cylinder, controlled by digital pulses supplied by the drive electronics 13. For example, the drive system may comprise an Olsen Linear Electro-hydraulic Pulse Drive Model No. LS300 manufactured by Olsen Control, Inc., Bristol, Conn., and described in U.S. Pat. No. 3,899,956. The Control 13 which includes the piston drive electronics as a programmer/controller may be a microcomputer such as the MCS40 microcomputer available from Intel Corporation. Guide rods 15 and 16 mounted between base support 17 and top support 18 guide the crosshead 19. The drive system drives the crosshead 19 at a constant rate independent of the loading effects of the material under test. Framing members 20 and 21 support the various components. The cassette "moving" member 8, comprises an air cylinder and indexing arm as better seen in FIG. 2, controls the movement of the cassette. The piston 22 is mounted to the crosshead via insulator 6 and is driven by the crosshead 19 into the barrel assembly 23 to extrude strand 24 of test material. The stress electronics 25 measure the force required to extrude the tire material.

Figure 2:
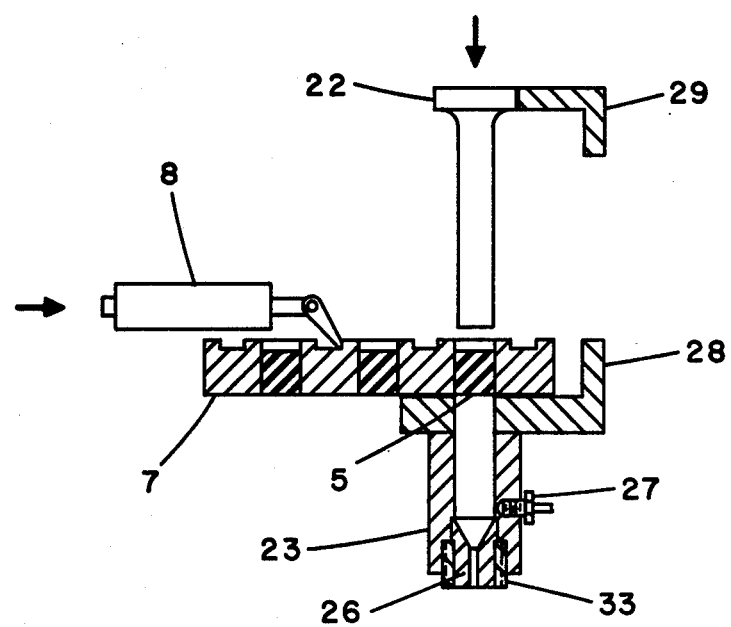
FIG. 2 is a sectional view of the tester and automatic feeding arrangement.

As better seen in FIG. 2, the cassette 7 is transported sequentially by mechanism 8 placing the samples under the piston 22. A thermal system comprising temperature controllers (not shown) and heated chamber maintains the barrel 23 and orifice 26 at a predetermined temperature (35°-290° C). A heated piston 22 mounted on a moving crosshead 19 (FIG. I) under control of the electronics 13 (FIG. 1) drives the sample 5 into the barrel 23. The cassette 7 is preloaded with elastomer samples and usually pre-heated to the required test temperature. Following the pre-heat, the cassette is loaded into the tester under the command of the control electronics 13. The cassette advance mechanism 8 will move the sample in the cassette 7 to the test position, which is directly beneath the heated piston 22. FIG. 2 indicates the initial position with the piston 22 raised and the test sample 5 in place.

Figure 3A:
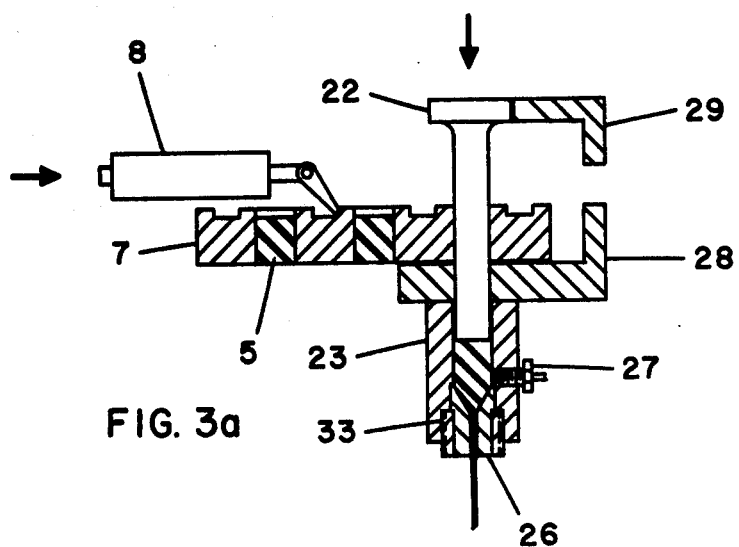
FIG. 3a is a sectional view of the tester during extrusion to evaluate viscosity by measuring force at constant shear rate and FIG. 3b is a typical stress and time plot of such extrusion.
Figure 3B:
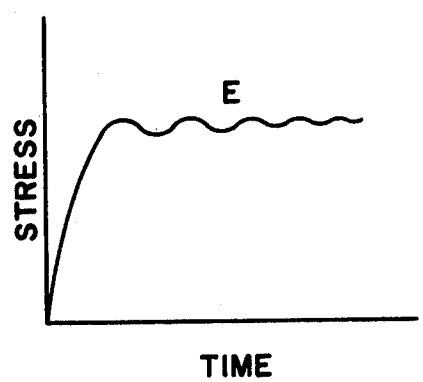

FIGS. 3 and 4 illustrate the transposition of the sample. In FIG. 3a, it can be seen that the sample under the applied force of the piston starts to extrude through the orifice 26 held in place by retaining nut 33. The pressure at the barrel is sensed by a pressure transducer 27 and an electronic signal is produced which is processed by the stress electronics 25 (FIG. 1) and can be displayed on a chart recorder 34 FIG. 6. An illustration of a typical recorder trace is shown in FIG. 3b, which shows the pressure (stress) plotted with respect to time. After a short period, the stress reaches a substantially constant value. The constant position of the curve represents the equilibrium value of stress E. Since the piston speed is constant, and corresponds to a pre-selected shear rate, the viscosity of the material is found for that shear rate. The piston continues to move down until a limit is imposed by the mechanical stops 28 and 29 coming in contact.

Figure 4A:
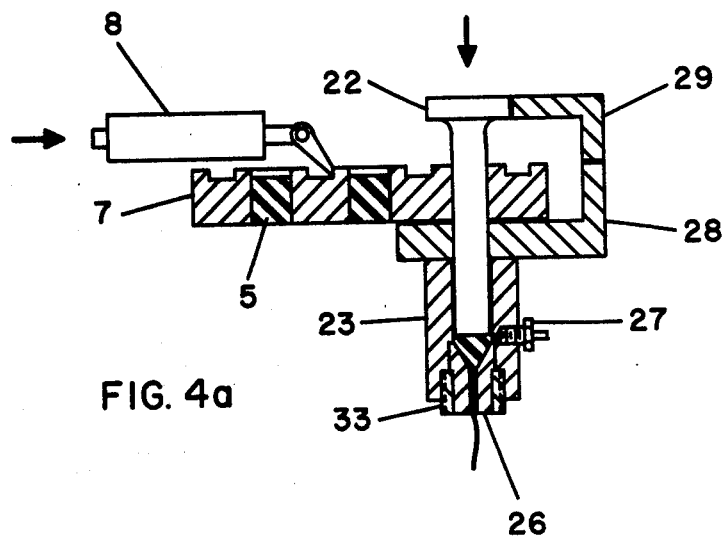
FIG. 4a is sectional view of the tester in operation during measurement of stress decay and FIG. 4b is typical stress and time plot of such measurement.
Figure 4B:
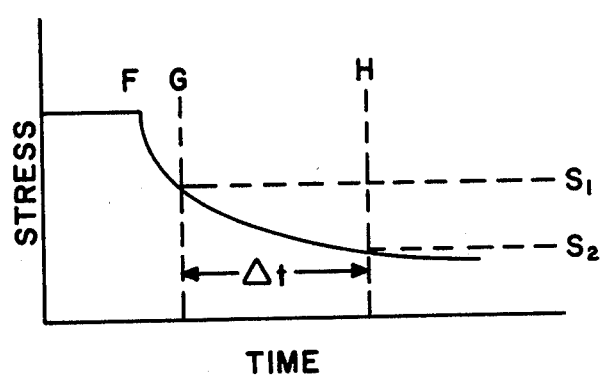

The stopped position is illustrated in FIG. 4a. At this point, the piston is locked in a fixed position by the pressure exerted upon it, and the action of the stops. Flow of the material continues under the constant force but the pressure decays at an approximate exponential rate. The decay is illustrated in FIG. 4b. Points S1 and S2 are preselected stress values which are set in the stress electronics. The stress relaxation curve F, G and H can be characterized by detecting the average time for the stress to fall from value S1 to S2.

Figure 5:
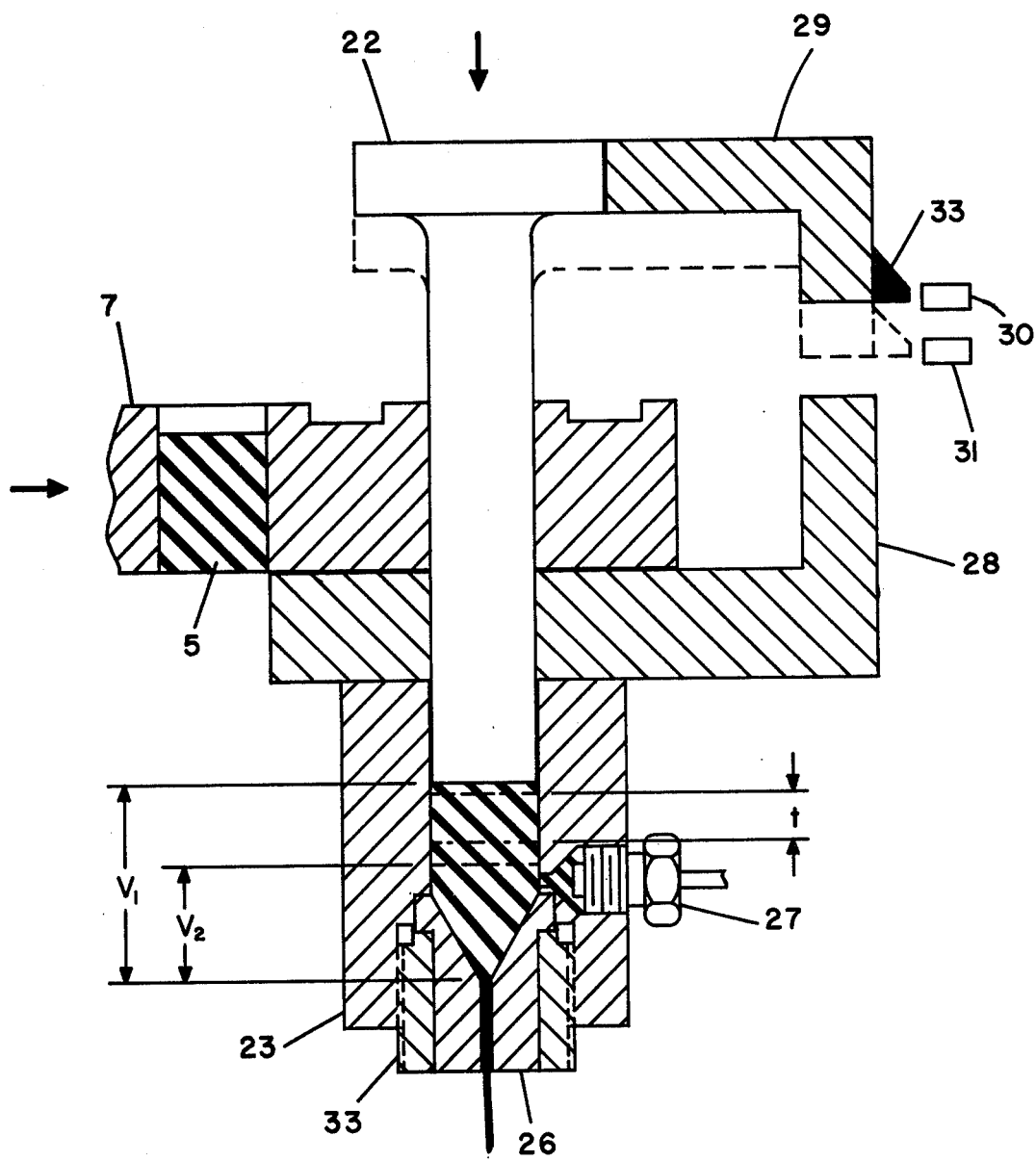
FIG. 5 is a sectional view of an alternate embodiment of tester during extrusion wherein viscosity is evaluated by measuring time to extrude a predetermined volume of material at constant force.

It has been found that the point at which the piston is stopped should correspond to a constant sample volume in the barrel, for example, the volume designated V2, FIG. 5, to enable reproducable results from different samples. $V_1$ in FIG. 5 illustrates the initial volume charge, which is not critical, although it should be sufficient to enable a constant stress level to be obtained consistent with the selected speed of the piston. The values corresponding to S1 and S2 can be selected to represent any two points on the relaxation curve, and will be selected to accommodate the wide range of elastomer characteristics.

The preceding description referred to a piston which was driven at a constant speed (shear rate). As an alternative the piston can be driven at a constant stress by an air cylinder, not shown. The speed of the piston will then vary and to obtain a measure of viscosity the average rate of travel (FIG. 5) for a known volume is measured. The measurement is accomplished by arranging preferably two optical electronic switches 30 and 31 spaced apart to represent a fixed sample volume. Alternatively, mechanical switches or any suitable means to detect a known volume could be used. The two switches 30 and 31 can be switched on by a light source 33 attached to the moving piston assembly. By coupling the switches to an electronic timer (part of control electronics), the time '*t*' is established. The relaxation method previously described remains unchanged for this mode. Apparent viscosity can be calculated from the equation:

$$n = Fr^3t/8R^2LV$$

F = Force on piston
r = orifice radius
R = barrel radius
L = orifice length
V = volume of material
t = extrusion time
Viscosity n = shear stress/shear rate It can be seen that the variables will be piston force F for a constant rate of travel and *t* for a constant stress mode. All other terms will be machine constants for given conditions. Hence, the electronic system can generate viscosity data for either drive alternative.

Figure 6:
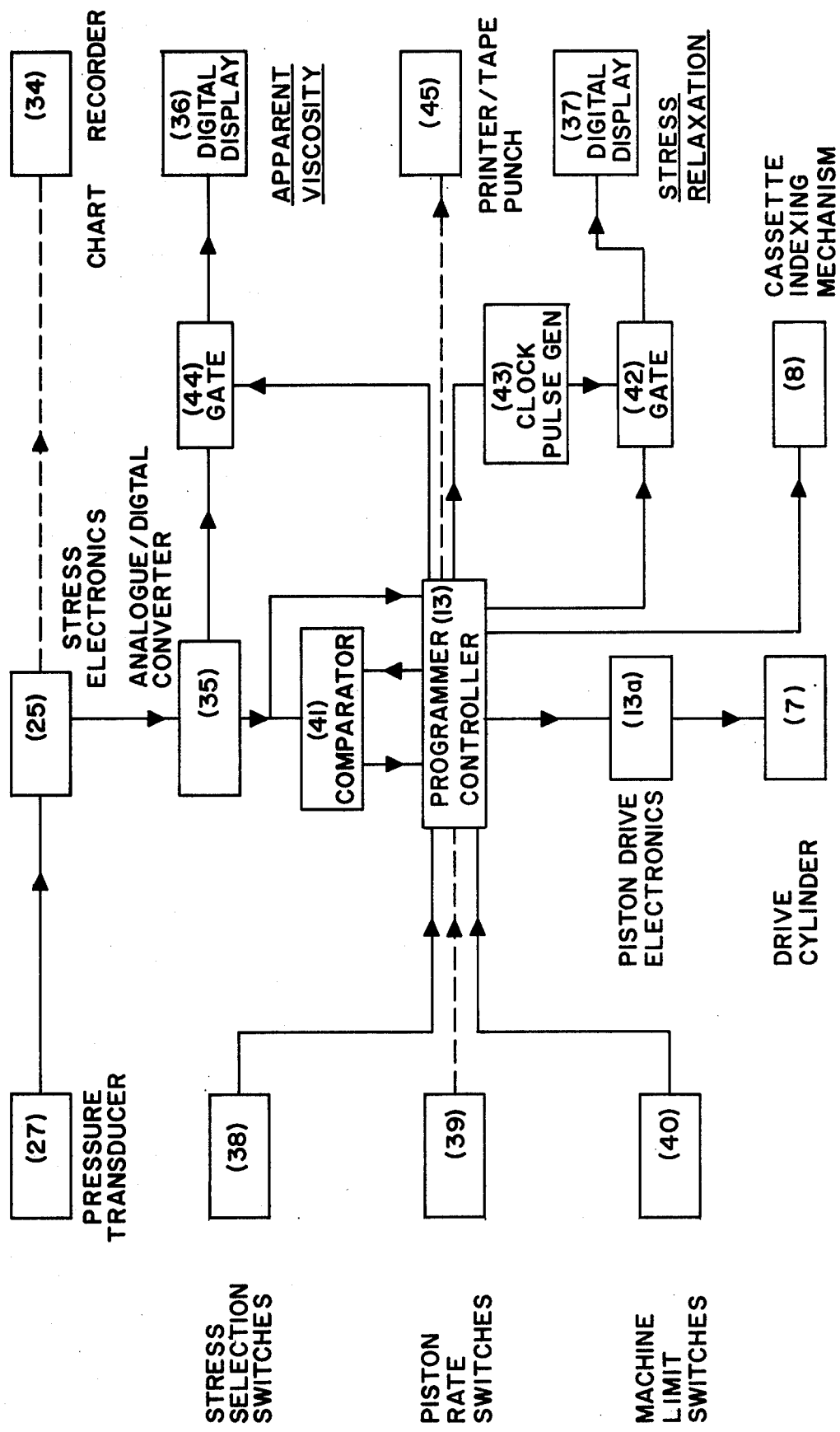
FIG. 6 is a schematic lay-out of the control and signal processing circuitry.

The control and signal processing circuitry are shown in greater detail in FIG. 6. In the embodiment illustrated, the drive system of the capillary rheometer is controlled by pulses to provide a constant rate of extrusion. The heart of the system is the programmer control 13 which in the preferred embodiment would be a micro-processor. The programmer controller 13 and piston drive electronics 13a are shown separately in FIG. 6; also, the function of blocks 35, 41, 42, 43 and 44 would be part of the processor function, but are shown separately to give a better understanding of the operation. The operation of a micro-processor is well known, a suitable type being the aforementioned Intel Model #MCS40. The functions of the various blocks can be described as follows:

At the start of the test sequence, a pulse from the programmer controller 13 will cause the Cassette Indexing Mechanism 8 to advance the cassette to the test station. At this point, the programmer will cause the piston 22 to move at a pre-selected rate which is determined and selected in the controller by selector means (not shown). The piston travel will continue downward and push the sample into the barrel of the test instrument. The pressure inside the barrel is monitored by the pressure transducer 27. The signals from the pressure transducer are fed to the stress electronics 25 and can be fed to a chart recorder 34 on which the resultant stress signal is plotted. The signal from the stress electronics is converted to a digital form by the analogue to digital converter 35 and at a defined point during the test corresponding to the equilibrium stress value shown in FIG. 3b the gate 44 will be enabled by the programmer controller to record the stress value for display in digital display 36. When the piston travel is finally limited by the mechanical stops 28, 29 (FIG. 2), then a second Digital Display 37 will begin to record the time for the stress to decay from S1 to S2 (FIG. 4b). The points corresponding to S1 and S2 are selected on the stress switches shown as in Block 38. The points which are selected by stress selection switches 38 are compared with the actual decaying stress signal by a comparitor 41 in conjunction with the programmer/controller 13. The gate 42 is enabled when the stress level corresponds to S1 and pulses from the pulse generator 43 will be fed to the Display 37 for a period determined by S2 minus S1. This value represents the stress relaxation time constant.

If desired, time constant limits or stress limits can be assigned in the micro-processor and the information displayed in 36 and 37 compared with such preselected limits. The limits and the actual test values may then be recorded on the printer tape punch 45. Furthermore, the values which are outside the preselected limits can be indicated. The points S1 and S2 provide a measure of the average slope of the stress decay curve. If more precise measure of the slope (average rate of stress decay) is required means may be included to differentiate the stress values over the selected period of stress decay. This can be accomplished by arranging a circuit such as that described in *Operational Amplifiers, Design and Application*, Burr Brown, page 220, FIG. 6.18, published by McGraw Hill. The output of the differentiating circuit can be displayed and will represent the instantaneous slope of the relaxation curve at a specific time interval. This would be controlled by the programmer 13 and displayed on 37. It will also be apparent that the tests may be conducted at a plurality of different shear rates resulting in different peak or equilibrium values of stress (and corresponding values for relaxation). Testing at a plurality of different shear rates may be programmed into the apparatus and can be performed automatically.

In the alternative embodiment described earlier and shown in FIG. 5, the viscosity is determined by the time for the piston to extrude a known volume of material. This time is controlled by the piston rate switches 39. In this case, the apparent viscosity will be the result of gating through gate 44 the required number of pulses corresponding to "t" (FIG. 5) the time to extrude a predetermined volume and will be displayed on 36. In either embodiment the addition of machine limit switches 40 is a desirable safety feature.

Although the invention has been illustrated by typical examples, it is not limited thereto. Changes and modifications of the examples of the invention herein chosen for purposes of disclosure can be made which do not constitute departure from the spirit and scope of the invention.

The embodiments of the invention in which an exclusive property or privilege is claimed are defined as follows:

1. In the method of evaluating an extrudable material by charging a supply of such material to a chamber having an outlet and movable member for forcing the material through the outlet and moving said member to force material from the outlet, the improvement which comprises stopping and securing the movable member at a predetermined position and measuring the force on the material as it decays with time.

2. In the method of evaluating an extrudable material by charging a supply of such material to a chamber having an outlet and movable member for forcing the material through the outlet the improvement which comprises in combination moving said member at a substantially constant rate to force material from the outlet, measuring the force required to extrude the material stopping and securing the movable member at a predetermined position and measuring the force on the material as it decays with time.

3. In the method of evaluating an extrudable material by charging a supply of such material to a chamber having an outlet and movable member for forcing the material through the outlet the improvement which comprises in combination moving said member at a substantially constant force to force material through the outlet, measuring the time required to extrude a predetermined volume of material stopping and securing the movable member at a predetermined position and measuring the force on the material as it decays with time.

4. In the method of evaluating an extrudable material by charging such material to a cylindrical chamber to which is attached an elongated circular outlet of smaller radius than the radius of the chamber and moving said member to force material from the outlet, the improvement which comprises stopping and securing the movable member at a predetermined position and measuring the force on the material in the chamber as it decays with time.

5. Apparatus for evaluating an extrudable material comprising in combination a supply chamber having an outlet and a movable member for forcing material through the outlet, means for moving said member to force material from the outlet, means for stopping the movable member and locking it in its place at a predetermined position and means for measuring the stress on the material.

6. Apparatus of claim 5 which includes means automatically to present samples of test material to the supply chamber.

7. Apparatus of claim 5 which includes means to determine the average rate of the stress decay.

8. Apparatus of claim 5 which includes means for moving said member at a plurality of preselected different substantially constant rates or forces.

9. Apparatus of claim 5 which includes means to compare time or stress values with preselected limits.

10. Apparatus of claim 5 in which the supply chamber is cylindrical and the outlet is an elongated circular member of smaller radius than the radius of the chamber and the means for measuring the stress on the material is a stress transducer which senses force in the cylindrical chamber.

* * * * *